(12) United States Patent
Nagahara et al.

(10) Patent No.: US 7,565,842 B2
(45) Date of Patent: Jul. 28, 2009

(54) ULTRASONIC RECEIVER

(75) Inventors: Hidetomo Nagahara, Kyoto (JP);
Masahiko Hashimoto, Osaka (JP);
Takehiko Suginouchi, Kyoto (JP)

(73) Assignee: Panasonic Corporation, Kadoma (JP)

( * ) Notice: Subject to any disclaimer, the term of this patent is extended or adjusted under 35 U.S.C. 154(b) by 52 days.

(21) Appl. No.: 11/996,529

(22) PCT Filed: May 10, 2007

(86) PCT No.: PCT/JP2007/059655

§ 371 (c)(1),
(2), (4) Date: Jan. 23, 2008

(87) PCT Pub. No.: WO2007/132728

PCT Pub. Date: Nov. 22, 2007

(65) Prior Publication Data

US 2008/0163691 A1    Jul. 10, 2008

(30) Foreign Application Priority Data

May 11, 2006   (JP) .............................. 2006-132161

(51) Int. Cl.
*G01N 29/28* (2006.01)
(52) U.S. Cl. .......................................... 73/617; 73/644
(58) Field of Classification Search .................. 73/617, 73/644
See application file for complete search history.

(56) References Cited

U.S. PATENT DOCUMENTS 4,091,891 A * 5/1978 Hino et al. .................. 181/185
4,442,512 A * 4/1984 Kodera et al. ................. 367/87
6,087,760 A * 7/2000 Yamaguchi et al. ......... 310/334
6,975,735 B1 * 12/2005 Kinoshita .................... 381/163

(Continued)

FOREIGN PATENT DOCUMENTS

JP        58-195884      12/1983

(Continued)

OTHER PUBLICATIONS

International Search Report for corresponding Application No. PCT/JP2007/059655 dated Aug. 7, 2007.

*Primary Examiner*—Hezron Williams
*Assistant Examiner*—Rose M Miller
(74) *Attorney, Agent, or Firm*—Renner, Otto, Boisselle & Sklar, LLP

(57) ABSTRACT

An ultrasonic receiver according to the present invention includes a first horn having a first large opening and a first small opening which are an incidence end and an outgoing end of an ultrasonic wave; a second horn having a second small opening and a second large opening which are an incidence end and an outgoing end of the ultrasonic wave, the first and second horns being located such that the first and second small openings face each other, and such that propagation directions of the ultrasonic wave in the first and second horns match each other; and at least one ultrasonic receiver main body provided between the first and second small openings, the ultrasonic receiver including a surface parallel to the propagation direction and detecting the ultrasonic wave which has propagated in the first horn and then is incident on the parallel surface. A cross-sectional area vertical to the propagation direction in the first horn decreases from the first large opening toward the first small opening; and a cross-sectional area vertical to the propagation direction in the second horn increases from the second small opening toward the second large opening.

8 Claims, 10 Drawing Sheets

U.S. PATENT DOCUMENTS 7,162,930 B2 1/2007 Hashimoto et al.
2005/0139013 A1 6/2005 Hashimoto et al.

FOREIGN PATENT DOCUMENTS

| JP | 03-113386 | 5/1991 |
| JP | 05-292598 | 11/1993 |
| JP | 08-194051 | 7/1996 |
| JP | 2003-139591 | 5/2003 |

* cited by examiner

ULTRASONIC RECEIVER

TECHNICAL FIELD

The present invention relates to an ultrasonic receiver for receiving an ultrasonic wave, which is capable of detecting the ultrasonic wave at high sensitivity and high accuracy.

BACKGROUND ART

Ultrasonic waves propagate through various mediums including gas, liquid and solid mediums and so are used in various fields including measurement, physical property measurement, engineering, medicine and biology.

Ease of propagation of an ultrasonic wave at an interface between different mediums is represented as an acoustic impedance ratio. In general, an ultrasonic wave is mostly reflected by an interface between mediums having significantly different levels of acoustic impedance, such as an interface between a gas and a solid, and cannot propagate to a different medium at high efficiency.

For detecting an ultrasonic wave, an ultrasonic vibrator is widely used, which includes a piezoelectric element formed of ceramics or the like. Therefore, when an ultrasonic wave which has propagated through a gas is to be detected by an ultrasonic vibrator, the ultrasonic wave which has propagated is mostly reflected by a surface of the ultrasonic vibrator and is only partially detected by the ultrasonic vibrator. This makes it generally difficult to detect an ultrasonic wave at high sensitivity. When an ultrasonic wave is transmitted from an ultrasonic vibrator to a gas also, the propagation efficiency is reduced by the reflection. Accordingly, when using an ultrasonic wave specifically for measuring a distance or flow rate or for detecting physical properties, how to detect an ultrasonic wave at high sensitivity is one of important issues.

In order to solve this problem, Patent Document 1, for example, discloses an ultrasonic transmitter/receiver main body capable of transmitting and receiving an ultrasonic wave at high efficiency in a wide band, using refraction of an ultrasonic wave in a gas. Hereinafter, this ultrasonic transmitter/receiver main body will be described.

As shown in FIG. 8, this conventional ultrasonic transmitter/receiver main body 101 includes an ultrasonic vibrator 2 and a propagation medium section 3 provided on a wave receiving face of the ultrasonic vibrator 2. A space around the ultrasonic transmitter/receiver main body 101 is filled with, for example, a fluid 4, for example, air. An interface between the ultrasonic vibrator 2 and the propagation medium section 3 will be referred to as a first surface area 31, and an interface between the propagation medium section 3 and the fluid 4 will be referred to as a second surface area 32. An angle made by the first surface area 31 and the second surface area 32 is represented with θ1, and an angle made by the normal to the second surface area 32 and a traveling direction of an ultrasonic wave is represented with θ2. X, Y and Z directions are set as shown in FIG. 8.

An ultrasonic wave is transmitted as follows. An electric signal is given to the ultrasonic vibrator 2 from a driving circuit (not shown), and the ultrasonic vibrator 2 is vibrated to generate an ultrasonic wave. The ultrasonic wave generated in the ultrasonic vibrator 2 propagates from the first surface area 31 toward the second surface area 32 through the transmission medium section 3 in a positive Y axial direction. Upon arriving at the second surface area 32, the ultrasonic wave changes the propagation direction thereof in conformity to the law of refraction, and propagates in the direction of an ultrasonic transmission path 5 in the fluid 4.

An ultrasonic wave is received as follows, i.e., oppositely to the manner of transmission. The ultrasonic wave, which has propagated through the fluid 4 filling the space around the ultrasonic transmitter/receiver main body 101, reaches the second surface area 32 and is refracted and transmitted through the propagation medium section 3. Then, the ultrasonic wave propagates through the propagation medium section 3 in a negative Y axis direction and reaches the ultrasonic vibrator 2. Upon reaching the ultrasonic vibrator 2, the ultrasonic wave deforms the piezoelectric element of the ultrasonic vibrator 2 to generate a potential difference between the electrodes and is detected by a receiving circuit (not shown).

As described above, the ultrasonic wave is refracted at the interface between the propagation medium section 3 and the fluid 4. Such a type of ultrasonic transmitter/receiver main body is specifically called an "oblique propagation type ultrasonic transmitter/receiver main body". In the ultrasonic transmitter/receiver main body 101, even where the fluid 4 is a medium having a very low level of acoustic impedance (sonic velocity in the medium×density of the medium) such as air or the like, the ultrasonic wave can be incident on the propagation medium section 3 from the fluid 4 at high efficiency, or can go out from the propagation medium section 3 to the fluid 4 at high efficiency.

Where the sonic velocities of the ultrasonic wave in the propagation medium section 3 and the fluid 4 are $C_1$ and $C_2$, and the densities of the propagation medium section 3 and the fluid 4 are $\rho_1$ and $\rho_2$, reflectance R of the ultrasonic wave at the interface between the second surface area 32 and the fluid 4 is represented by the following expression (1).

[Expression 1]

$$R = \frac{\frac{\rho_2}{\rho_1} - \frac{\tan\theta_1}{\tan\theta_2}}{\frac{\rho_2}{\rho_1} + \frac{\tan\theta_1}{\tan\theta_2}} \tag{1}$$

In the case where $C_1$, $C_2$, $\rho_1$ and $\rho_2$ fulfill the following expression (2), the values of $\theta_1$ and $\theta_2$ with which the numerator of expression (1) is zero necessarily exist. Namely, the reflectance R is zero.

[Expression 2]

$$\frac{\rho_2}{\rho_1} < \frac{C_1}{C_2} < 1 \tag{2}$$

$\theta_1$ and $\theta_2$ fulfill expression (3) (Snell's law).

[Expression 3]

$$\frac{\sin\theta_1}{C_1} = \frac{\sin\theta_2}{C_2} \tag{3}$$

As a condition for $\theta_1$ under which the reflectance R is zero, expression (4) is obtained using expression (3).

[Expression 4]

$$\tan^2\theta_1 = \frac{\left(\frac{\rho_2}{\rho_1}\right)^2 - \left(\frac{C_1}{C_2}\right)^2}{\left(\frac{C_1}{C_2}\right)^2 - 1} \tag{4}$$

Namely, as shown in Patent Document 1, when expression (2) is fulfilled in the oblique propagation type ultrasonic transmitter/receiver main body, there exists a direction (angle $\theta_1$) in which the transmission efficiency of the ultrasonic wave at the second surface area 32 can be approximately 1. The angle $\theta_1$ made by the first surface area 31 and the second surface area 32 at this point is represented by expression (4). Expressions (1) and (4) do not heavily rely on the frequency of the propagating ultrasonic wave. Therefore, the oblique propagation type ultrasonic transmitter/receiver main body 101 capable of transmitting and receiving an ultrasonic wave at high efficiency and in a wide band is realized.

Patent Document 1: United States Laid-Open Patent Publication No. 2005/0139013

Patent Document 2: Japanese Laid-Open Utility Model Publication No. 58-195884

Patent Document 3: Japanese Laid-Open Patent Publication No. 5-292598

DISCLOSURE OF THE INVENTION

Problems to be Solved by the Invention

According to Patent Document 1, in order to allow the oblique propagation type ultrasonic transmitter/receiver main body 101 to receive an ultrasonic wave at high efficiency, expression (2) needs to be fulfilled and the ultrasonic propagating through the fluid 4 needs to be incident at angle $\theta_2$ with respect to the normal to the second surface area 32.

Therefore, as shown in FIG. 9, even if, for example, the ultrasonic wave propagates through zones L2, L3 and L4 of the fluid 4, only an ultrasonic wave component propagating through the zone L3 reaches the second surface area 32 whereas the ultrasonic wave components propagating through the zones L2 and L4 do not reach the second surface area 32. Namely, among the ultrasonic wave propagating through the zones L2, L3 and L4, only the ultrasonic wave component propagating through the zone L3 is received by the oblique propagation type ultrasonic transmitter/receiver main body 101.

The ultrasonic wave which has propagated through the zone L3 of the fluid 4 is transmitted through the second surface area 32 and is detected by the ultrasonic vibrator 2 located in a zone L1. Since the zone L1 is significantly larger than the zone L3 (L3<<L1), the ultrasonic wave received by the oblique propagation type ultrasonic transmitter/receiver main body 101 is diffused in the second transfer area 32 before reaching the ultrasonic vibrator 2. Therefore, at the time when the ultrasonic wave is received by the oblique propagation type ultrasonic transmitter/receiver main body 101, the energy density of the ultrasonic wave is reduced. This results in the problem that the receiving sensitivity of the oblique propagation type ultrasonic transmitter/receiver main body 101 is low.

This problem is common among ultrasonic receivers which receive an ultrasonic wave propagating in a direction which is not vertical to the ultrasonic wave receiving face. The present invention has an object of solving such a problem of the conventional art and providing an ultrasonic receiver capable of receiving an ultrasonic wave at high sensitivity.

Means for Solving the Problems

An ultrasonic receiver according to the present invention includes a first horn having a first large opening which is an ultrasonic incidence end and a first small opening which is an ultrasonic outgoing end; a second horn having a second small opening which is an ultrasonic incidence end and a second large opening which is an ultrasonic outgoing end, the second horn being located such that the first small opening of the first horn and the second small opening of the second horn face each other, and such that a first propagation direction of an ultrasonic wave propagating in the first horn and a second propagation direction of the ultrasonic wave propagating in the second horn match each other; and at least one ultrasonic receiver main body provided between the first small opening of the first horn and the second small opening of the second horn, the ultrasonic receiver including a surface parallel to the first propagation direction and detecting the ultrasonic wave which has propagated in the first horn and then is incident on the parallel surface. A space in the first horn in which the ultrasonic wave propagates has a cross-sectional area, vertical to the first propagation direction, which decreases from the first large opening toward the first small opening; and a space in the second horn in which the ultrasonic wave propagates has a cross-sectional area, vertical to the second propagation direction, which increases from the second small opening toward the second large opening.

In one preferred embodiment, the ultrasonic receiver has a space passing through the first large opening of the first horn to the second large opening of the second horn.

In one preferred embodiment, in the first horn, the cross-sectional area, vertical to the first propagation direction, of the space through which the ultrasonic propagates exponentially decreases along a propagation direction from the first large opening to the first small opening.

In one preferred embodiment, in the second horn, the cross-sectional area, vertical to the second propagation direction, of the space through which the ultrasonic propagates exponentially increases along a propagation direction from the second small opening to the second large opening.

In one preferred embodiment, the at least one ultrasonic receiver main body includes an ultrasonic vibrator having a wave receiving face; and a propagation medium section having a first surface area and a second surface area. The first surface area of the propagation medium section is bonded with the wave receiving face of the ultrasonic vibrator, and the first surface area of the propagation medium section forms the parallel surface.

In one preferred embodiment, the relationship of $(\rho_2/\rho_1) < (C_1/C_2) < 1$ is fulfilled where $\rho_1$ and $\rho_2$ are densities of the propagation medium section and a fluid filling a space around the at least one ultrasonic receiver main body, and $C_1$ and $C_2$ are sonic velocities of the ultrasonic wave in the propagation medium section and the fluid filling the space.

In one preferred embodiment, the propagation medium section is formed of an dry gel formed of an inorganic material or an organic polymer material.

An ultrasonic receiver according to the present invention includes a first horn having a first large opening which is an ultrasonic incidence end and a first small opening which is an ultrasonic outgoing end; at least one ultrasonic receiver main body provided adjacent to the first small opening, the ultrasonic receiver including a surface parallel to a first propagation direction in which an ultrasonic wave propagates in the first horn, and detecting the ultrasonic wave which has propagated in the first horn and then is incident on the parallel surface; and an acoustic impedance transformer for holding a fluid fulfilling a space around the at least one ultrasonic receiver main body such that an acoustic impedance of the fluid gradually changes, the acoustic impedance transformer being provided such that the ultrasonic receiver main body is held between the first horn and the acoustic impedance transformer. A space in the first horn in which the ultrasonic wave propagates has a cross-sectional area, vertical to the first propagation direction, which increases from the first small opening toward the first large opening.

EFFECTS OF THE INVENTION

According to the present invention, the energy of the ultrasonic wave is increased by the first horn, and the ultrasonic wave having a higher sound pressure is detected by the ultrasonic receiver main body. For the detection, an oblique propagation type ultrasonic receiver main body, which is highly efficient, is used. In addition, the second horn allows the ultrasonic wave, which was not received by the ultrasonic receiver main body, to go outside without being reflected. Accordingly, the present invention realizes an ultrasonic receiver capable of detecting an ultrasonic wave at high sensitivity, high efficiency and high accuracy.

DESCRIPTION OF THE REFERENCE NUMERALS

Figure 1:
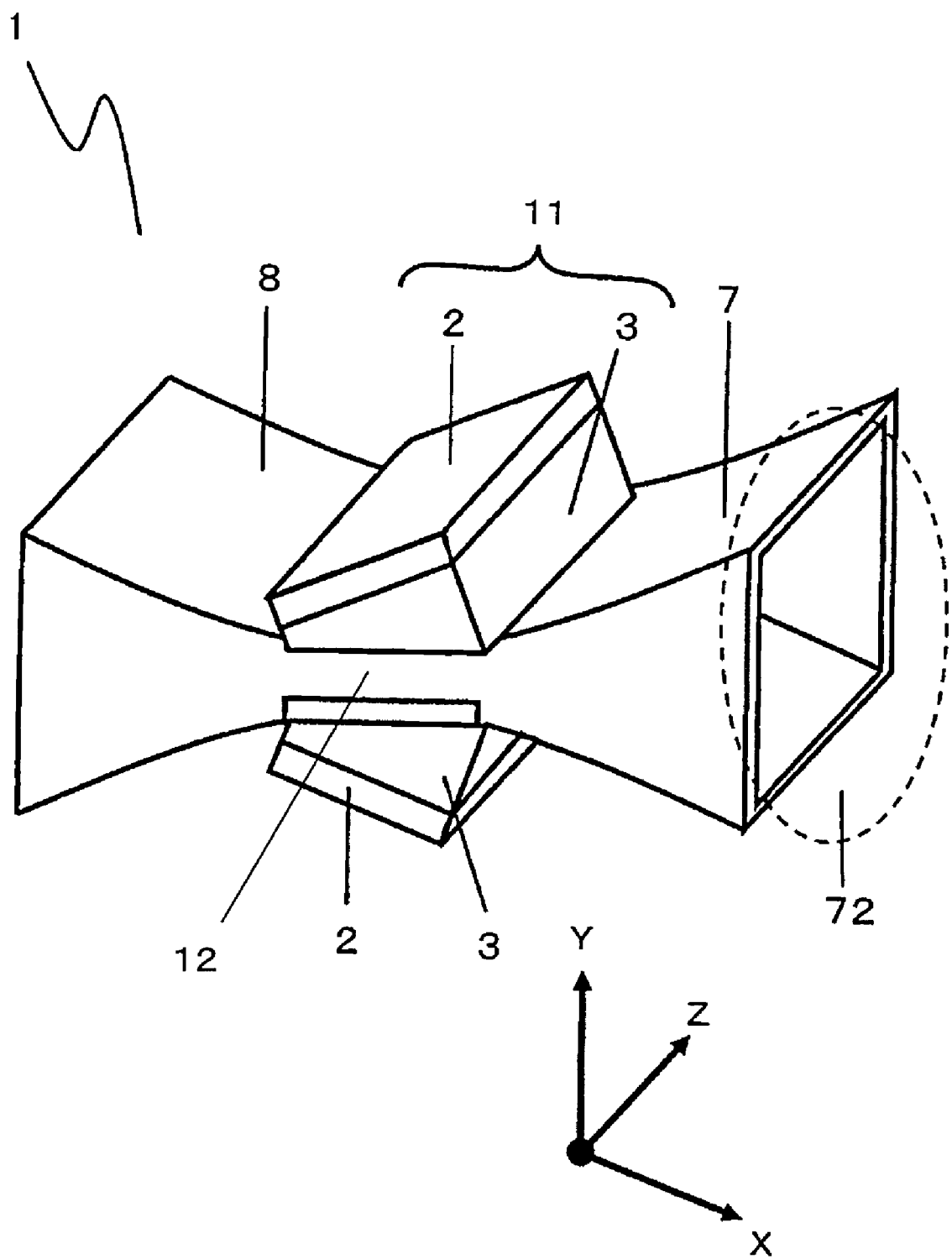
FIG. 1 an isometric view showing an ultrasonic receiver in an embodiment according to the present invention.

1 Ultrasonic receiver
2 Ultrasonic vibrator
3 Propagation medium section
4 Fluid
5 Ultrasonic propagation path
6 Horn
7 First horn
8 Second horn
9 Convergence end
10 Connecting member
11 Ultrasonic receiver main body
31 First surface area
32 Second surface area
71 First small opening
72 First large opening
81 Second large opening
82 Second small opening
101 Ultrasonic transmitter/receiver main body
201 Ultrasonic receiver having one horn
202 Ultrasonic receiver having one horn

BEST MODE FOR CARRYING OUT THE INVENTION

In order to improve the receiving sensitivity of an ultrasonic receiver which receives an ultrasonic wave propagating in a direction which is not vertical to the ultrasonic wave receiving face, the present inventors examined ultrasonic receivers using a horn or a cone.

It is conventionally known to use a horn or a cone to improve the directivity of the ultrasonic wave received or transmitted by an ultrasonic receiver. For example, Patent Document 2 discloses an ultrasonic sensor attachable to a lawn mower capable of unattended traveling. The ultrasonic sensor disclosed in this publication includes a pair of horns opened forward and rearward in an advancing direction of the lawn mower and a shielding body for selectively shielding an end portion of one of the pair of horns in accordance with the traveling direction of the lawn mower.

Figure 10:
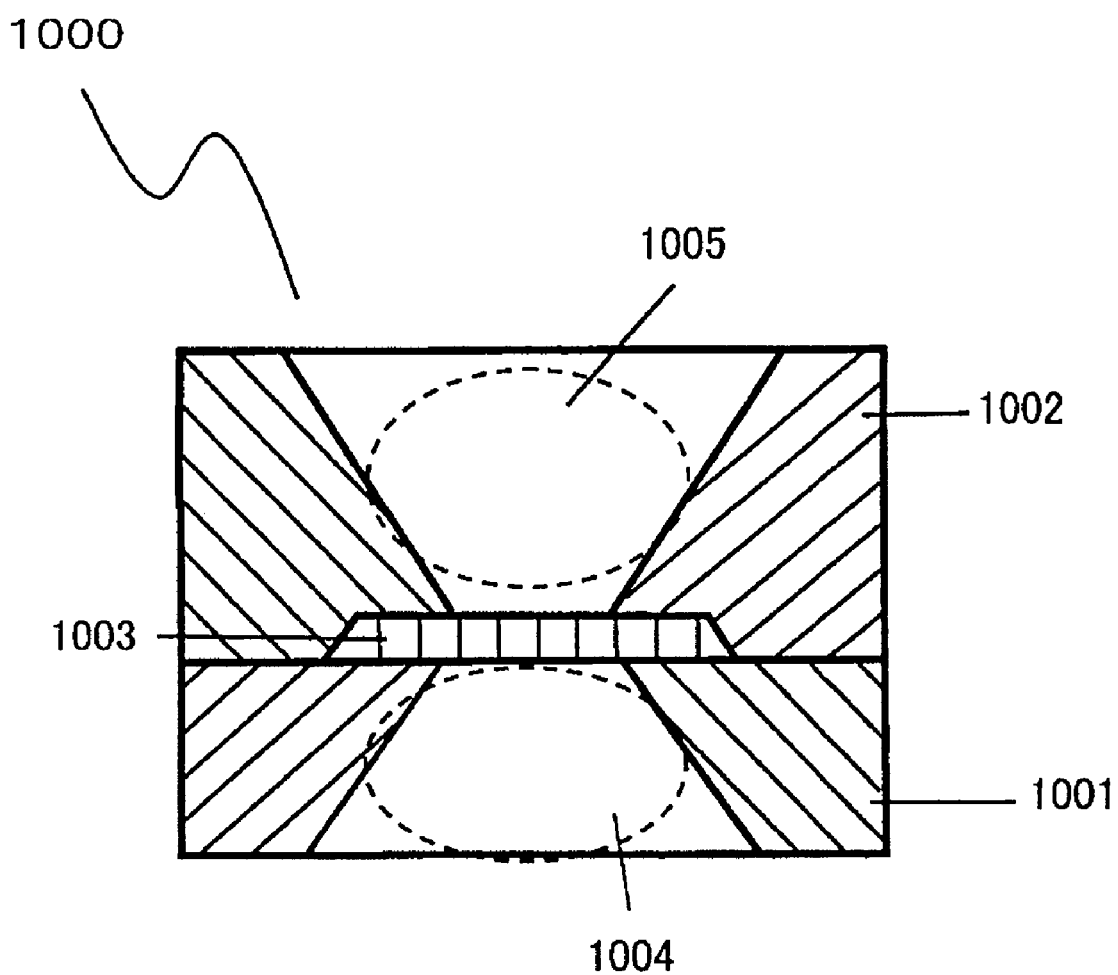
FIG. 10 is a cross-sectional view showing a conventional sonic wave transducer.

Patent Document 3 discloses a sonic wave transducer 1000 shown in FIG. 10 including a horn formed by precision processing of silicon. The sonic wave transducer 1000 includes a base 1001, a piezoelectric element 1003 supported by the base 1001, and a horn 1002 having an opening 1005. The horn 1002 is used for improving the directivity of the sonic wave. The base 1001 has an opening 1004 for allowing the piezoelectric element 1003 to vibrate easily.

Figure 11:
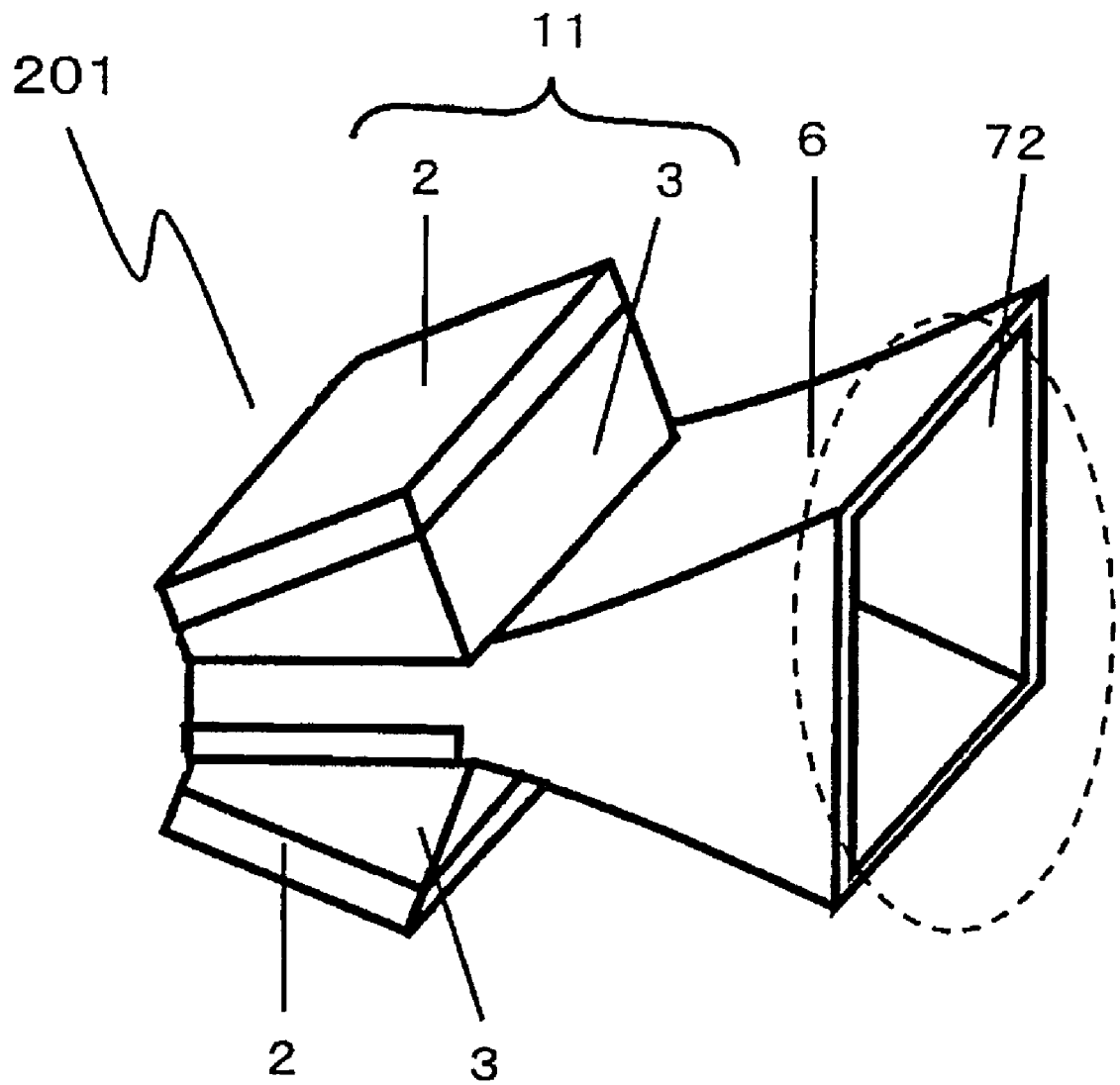
FIG. 11 is an isometric view of an ultrasonic receiver illustrating a problem to be solved by the present invention.
Figure 11:
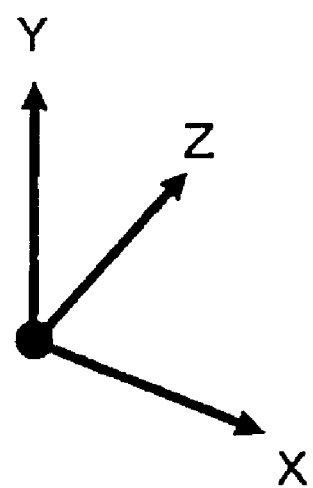
Figure 12:
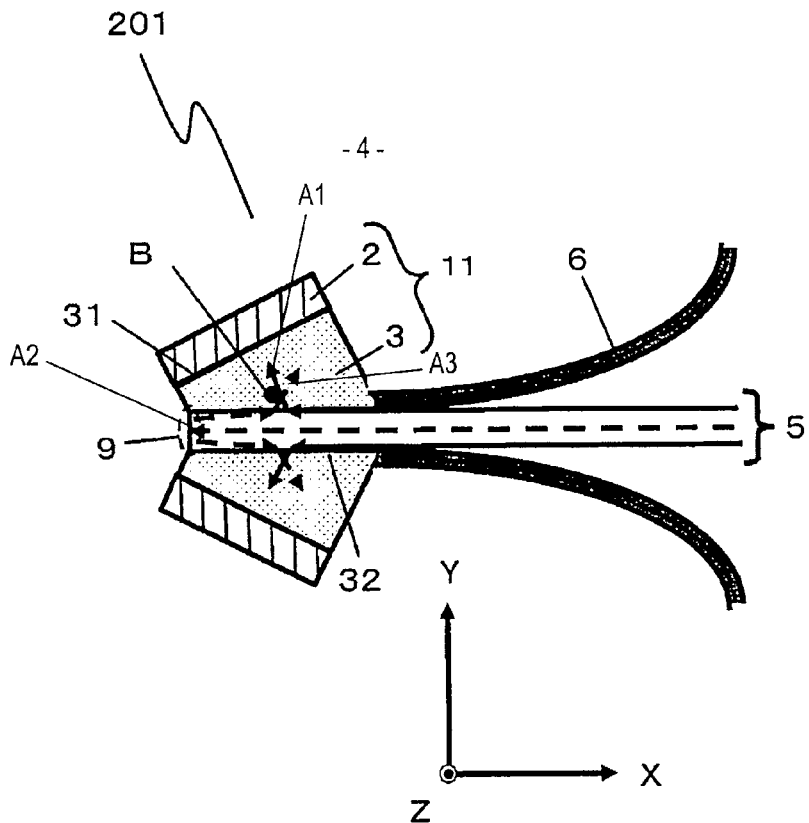
FIG. 12 is a cross-sectional view of the ultrasonic receiver shown in FIG. 11 taken along plane XY.

In Patent Documents 2 and 3, a horn is used for improving the directivity. Since the opening of the horn can be made larger than the wave receiving face of the ultrasonic vibrator, the horn can be used to improve the energy density of the ultrasonic wave. Accordingly, an ultrasonic receiver which combines the horn and the oblique propagation type ultrasonic transmitter/receiver main body is considered to alleviate the poorness in the receiving sensitivity. FIG. 11 is an isometric view of an ultrasonic receiver 201 proposed by the present inventor which includes a horn 6 and oblique propagation type ultrasonic receiver main bodies 11 attached thereto. FIG. 12 is a cross-sectional view of FIG. 11 taken along plane XY.

As shown in FIG. 11 and FIG. 12, a YZ cross-sectional area of an inner space of the horn 6 having a large opening 72 decreases along a negative X axial direction. A pair of ultrasonic receiver main bodies 11 are connected to a narrowed end of the inner space of the horn 6. The pair of ultrasonic receiver main bodies 11 are located such that the second surface areas 32 thereof are parallel to a direction in which the ultrasonic wave propagates in an X axial direction in the horn 6. The pair of ultrasonic receiver main bodies 11 receive the ultrasonic wave from the second surface areas 32. As shown in FIG. 12, a left end in the X axial direction of a space formed by the horn 6 and the ultrasonic receiver main bodies 11 is closed. This left end will be referred to as a "convergence end 9".

The ultrasonic wave which has propagated from a positive X side in FIG. 12 is incident on the large opening 72 of the horn 6. The ultrasonic wave propagates in a negative X axial direction in the horn 6. Then, the ultrasonic wave is converged by an effect provided by the shape of the horn 6, and thus the energy density thereof is increased.

The ultrasonic wave which has passed through the horn 6 reaches a surface of each propagation medium section 3. Among the ultrasonic wave which has reached the surface of each propagation medium section 3, an ultrasonic wave component traveling in a direction making angle $\theta_2$ with the second surface area 32 propagates through the propagation medium section 3 as represented with solid arrow A1. Then, the ultrasonic wave propagates to each ultrasonic vibrator 2, and the ultrasonic vibrator 2 converts the ultrasonic wave into an electric signal.

However, as long as the propagation medium section 3 has a finite size, it is impossible that the entirety of the ultrasonic wave which has propagated in the horn 6 is transmitted through the propagation medium section 3. As represented with dashed arrow A2 in FIG. 12 as an example, there occurs an ultrasonic wave component which is not transmitted through the propagation medium section 3.

The ultrasonic wave component which is not transmitted through the propagation medium section 3 is reflected by the convergence end 9 and then propagates in the horn 6 back in the positive X axial direction. A part of the ultrasonic wave which is reflected by the convergence end 9 and propagates back in the positive X axial direction makes angle $\theta_2$ with the second surface area 32.

Ideally, such a reflected component of the ultrasonic wave should not be received, but is actually received by the ultrasonic receiver main bodies 11 as represented by dashed arrow A3. An examination by the present inventor found that a problem of the structure including the ultrasonic transmitter/receiver main bodies 101 and the horn 6 attached thereto is that the ultrasonic wave reflected by the convergence end 9 is detected by the ultrasonic vibrator 2.

Figure 13:
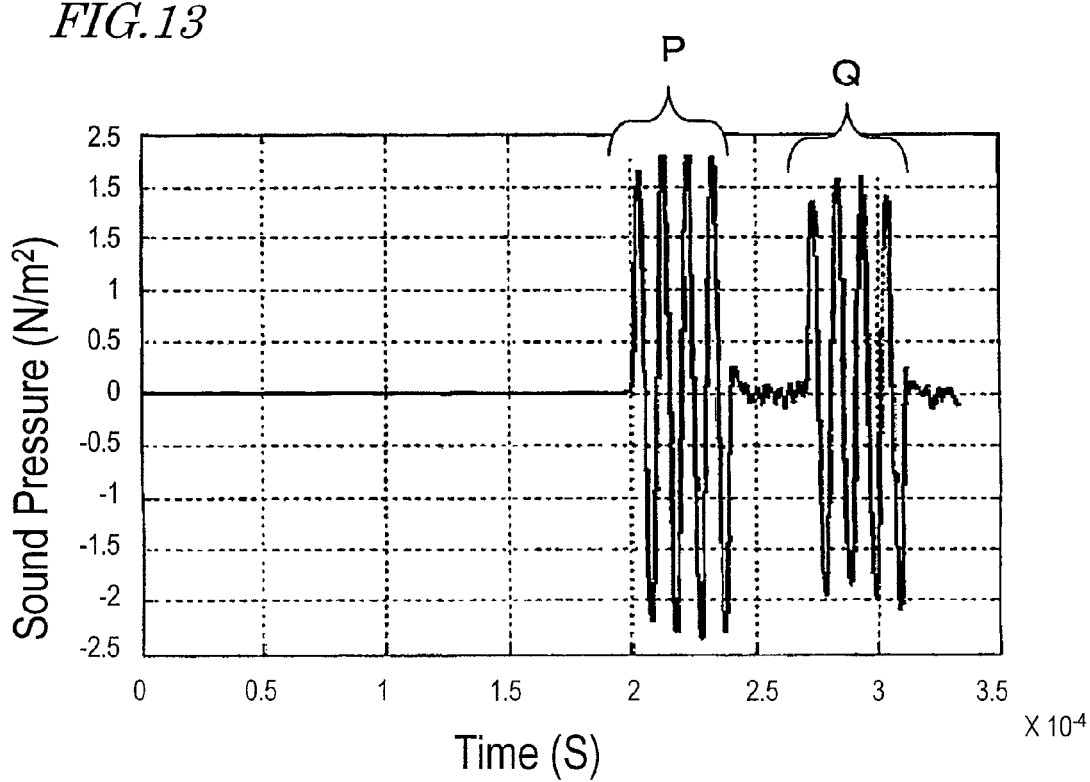
FIG. 13 is a graph showing a result of detecting an ultrasonic wave using the ultrasonic receiver shown in FIG. 11.

FIG. 13 shows a result of receiving, by the ultrasonic receiver 201 shown in FIG. 12, a 100 kHz four-peak burst ultrasonic wave propagating from the positive X axial side to the negative X axial side of the ultrasonic receiver 201 (FIG. 13 shows an over-time change in the sound pressure at point B in FIG. 12). In FIG. 13, the horizontal axis represents the time, and the vertical axis represents the sound pressure. As shown in FIG. 13, first, an ultrasonic wave P incident on the large opening of the horn 6 and propagating in the negative X axial direction is detected, and then, an ultrasonic wave Q reflected by the convergence end 9 is detected. Ideally, only the ultrasonic wave which has propagated through the fluid 4 should be observed, and the ultrasonic wave Q should not be observed. If, at the time when the ultrasonic wave Q is observed, an ultrasonic wave is transmitted after ultrasonic wave P, the receiving signals are overlapped and accurate ultrasonic wave measurement cannot be performed.

Figure 14:
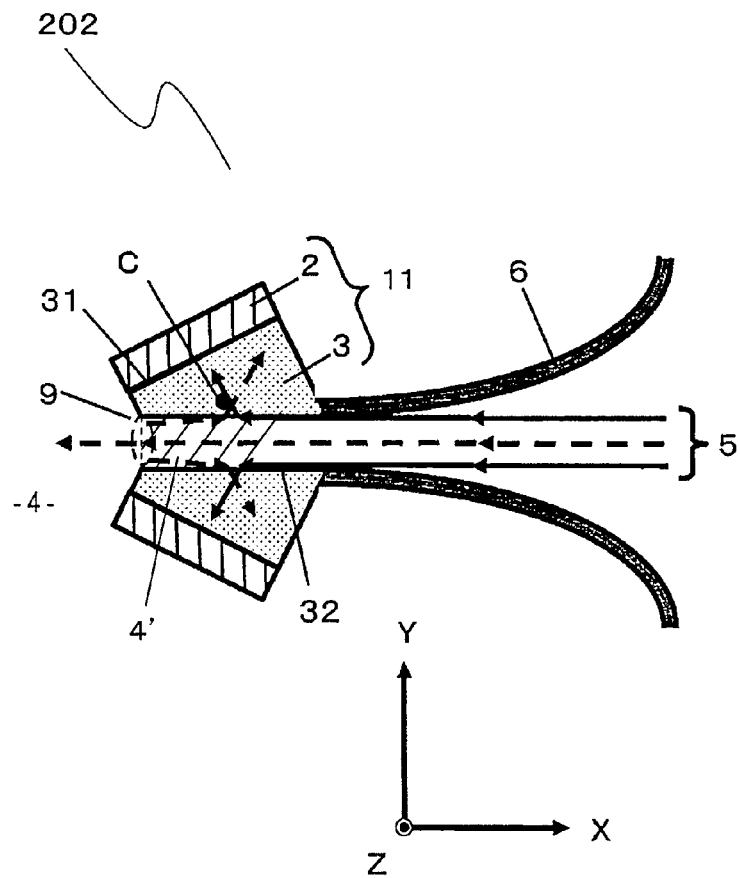
FIG. 14 is a cross-sectional view of another ultrasonic receiver illustrating a problem to be solved by the present invention.

In order to suppress the reflection of the ultrasonic wave at the convergence end 9, it is conceivable to open the convergence end 9 of the ultrasonic receiver 201. FIG. 14 is a cross-sectional view showing a structure of an ultrasonic receiver 202 having the convergence end 9 of the horn 6 being opened. The unit receiver 202 has the same structure as that of the ultrasonic receiver 201 in FIG. 11 and FIG. 12 except that the convergence end 9 is opened.

Figure 15:
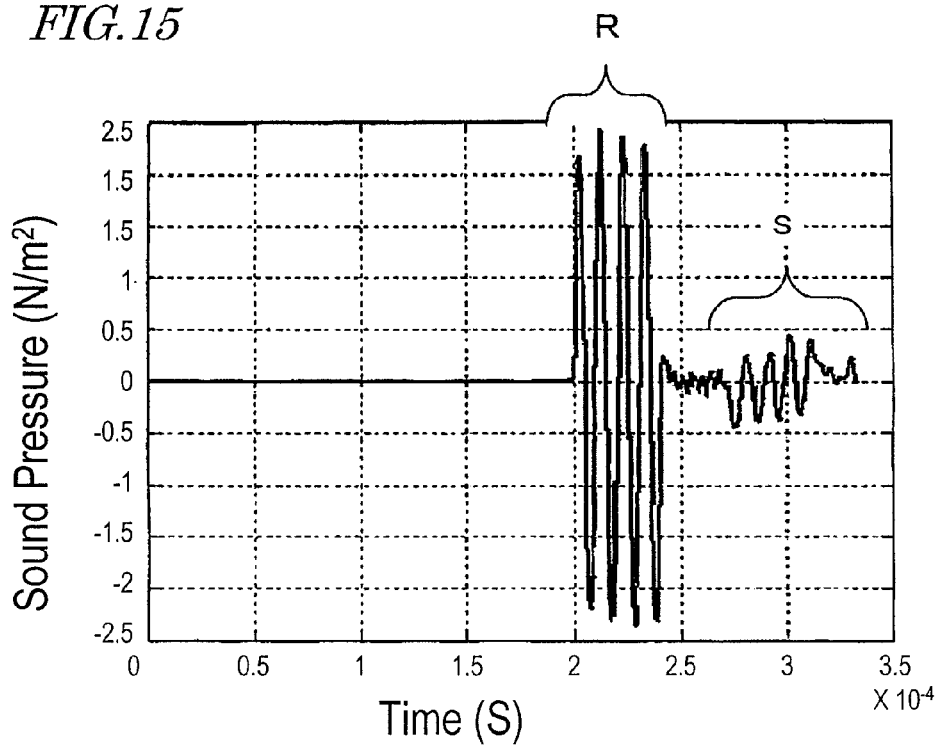
FIG. 15 is a graph showing a result of detecting an ultrasonic wave using the ultrasonic receiver shown in FIG. 14.

FIG. 15 shows a result of receiving, by the ultrasonic receiver 202 shown in FIG. 14, a 100 kHz four-peak burst ultrasonic wave propagating from the positive X axial side to the negative X axial side of the ultrasonic receiver 202 (FIG. 15 shows an over-time change in the sound pressure at point C in FIG. 14). In FIG. 15, the horizontal axis represents the time, and the vertical axis represents the sound pressure.

As shown in FIG. 15, first, the ultrasonic wave P incident on the large opening of the horn 6 and propagating in the negative X axial direction is detected, and then, an ultrasonic wave S having a disturbed waveform is detected. It is thus found that even by the ultrasonic receiver 202 having the opened convergence end 9, unnecessary ultrasonic waves are received and thus accurate ultrasonic wave measurement cannot be performed.

As a result of detailed examinations performed by the present inventor, it is considered that the unnecessary ultrasonic waves are received for the following reasons. Due to the size difference shown in FIG. 14 between the narrow space around a fluid 4' in the vicinity of the convergence end 9 of the horn 6 and the large open space around the fluid 4 outside the convergence end 9, the fluids 4 and 4' have difference levels of acoustic impedance. Therefore, the acoustic impedance becomes discontinuous at the convergence end 9, which causes reflection.

Based on such knowledge, the present inventor found that by providing, at the convergence 9, an acoustic impedance transformer for holding the fluid 4 such that the acoustic impedance gradually changes, unnecessary reflection at the convergence end 9 is suppressed and thus an ultrasonic receiver capable of accurate measurement is realized. Such a problem is not generated in the devices described in Patent Documents 2 and 3 including a sonic wave vibrator located vertical to the ultrasonic wave propagating in the horn.

Hereinafter, an ultrasonic receiver according to the present invention will be described with reference to the drawings.

Figure 2:
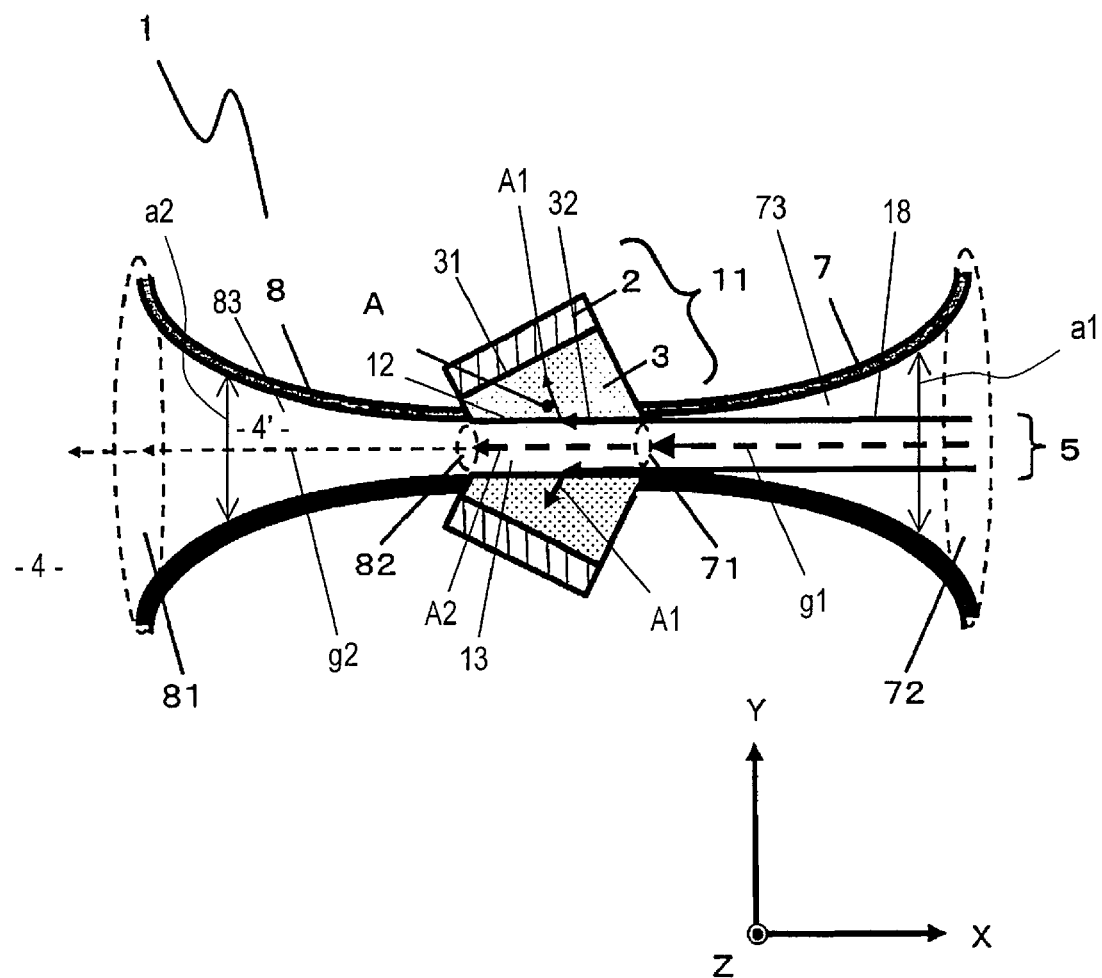
FIG. 2 is a cross-sectional view of the ultrasonic receiver shown in FIG. 1 taken along plane XY.

FIG. 1 is an isometric view of an ultrasonic receiver 1. XYZ directions are set as shown in FIG. 1. FIG. 2 shows a cross-section of the ultrasonic receiver 1 taken along plane XY.

The present invention is preferably usable to ultrasonic receivers used in various fields. In general, an ultrasonic receiver also acts as an ultrasonic transmitter. Therefore, the present invention at least encompasses a device capable of receiving an ultrasonic wave and further encompasses an ultrasonic receiver also capable of transmitting an ultrasonic wave. When transmitting an ultrasonic wave, however, the above-described reflection of the ultrasonic wave at the convergence end does not occur, and thus the effect of the acoustic impedance transformer is not provided.

As shown in FIG. 1 and FIG. 2, an ultrasonic receiver 1 includes a first horn 7, a second horn 8 and a pair of ultrasonic receiver main bodies 11.

The first horn 7 has a first space 73 having a first large opening 72 which is an ultrasonic incidence end and a first small opening 71 which is an ultrasonic outgoing end, on two ends thereof. The first large opening 72 is larger than the first small opening 71. The propagation direction of the ultrasonic wave which is incident on the first large opening 72 is controlled by the first space 73. Namely, the propagation direction in the first horn 7 is an axial direction in which the first space 73 extends. Specifically, the ultrasonic wave is controlled to propagate in a direction of arrow g1. In the first horn 7, a cross-sectional area a1 of the first space 73 vertical to the propagation direction g1 decreases from the first large opening 72 toward the first small opening 71. Owing to this, while the ultrasonic wave incident on the first large opening 72 propagates through the first space 73 in the propagation direction g1, the energy density of the ultrasonic wave is increased in accordance with the decrease in the cross-sectional area, and thus the sound pressure is raised.

More preferably, an inner surface of the first horn 7 which defines the first space 73 is curved in the propagation direction g1 such that the cross-sectional area a1 exponentially decreases along the propagation direction g1 from the first large opening 72 toward the first small opening 71. In this embodiment, as shown in FIG. 1, the first horn 7 has a constant width in the Z direction. In this case, the cross-sectional area is exponentially decreased along the propagation direction g1 by exponentially decreasing the width in the Y direction along the propagation direction g1.

Alternatively, the width of the first horn 7 in the Z direction may also be decreased from the first large opening 72 toward the first small opening 71. For example, the cross-sectional area a1 may be exponentially decreased by decreasing the width of the first horn 7 in the Y direction and the width thereof in the Z direction along the propagation direction g1 in proportion to $\sqrt{e}$. By exponentially decreasing the cross-sectional area a1 in this manner, the reflection of the ultrasonic wave in the first horn 7 can be minimized to compress the ultrasonic wave 5 with no phase disturbance and thus to raise the sound pressure.

There is no specific limitation on the external shape of the first horn 7 as long as having the first space 73 described above. For example, the first space 73 may have a block-type structure capable of forming a smooth face which does not substantially absorb an ultrasonic wave. In the case where the first horn 7 is formed of a plate material such as aluminum or a resin, the external shape of the first horn 7 reflects the shape of the first space 73. The first horn 7 having such a shape is occasionally referred to as a cone.

The second horn 8 has a second space 83 having a second small opening 82 which is an ultrasonic incidence end and a second large opening 81 which is an ultrasonic outgoing end, on two ends thereof. The second large opening 81 is larger than the second small opening 82. The propagation direction of the ultrasonic wave which is incident on the second small opening 82 is controlled by the second space 83. The propagation direction in the second horn 8 is also an axial direction in which the second space 83 extends. Specifically, the ultrasonic wave is controlled to propagate in a direction of arrow g2. In the second horn 8, a cross-sectional area a2 of the second space 83 vertical to the propagation direction g2 increases from the second small opening 82 toward the second large opening 81.

Owing to this, the cross-sectional area of the second space 83 can be gradually increased from the second small opening 82 toward the second large opening 81, and thus the level of acoustic impedance of the fluid 4' in the second space 83 can be gradually reduced to decrease the difference with the impedance of the fluid 4 outside the second horn 8. As a result, the component of the ultrasonic wave which is not taken into the ultrasonic receiver main bodies 11 is transmitted in the negative X axial direction, so that the ultrasonic wave is not taken into the propagation medium section 3. Since the level of acoustic impedance of the fluid 4' in the second space 83 gradually changes at this time, the reflection is suppressed from being caused by the mismatching of the impedance with that of the ultrasonic wave propagating in the negative X direction.

More preferably, an inner surface of the second horn 8 which defines the second space 83 is curved in the propagation direction g2 such that the cross-sectional area a2 exponentially increases along the propagation direction g2 from the second small opening 82 toward the second large opening 81. As with the first horn 7, in the case where the second horn 8 has a constant width in the Z direction, the width thereof in the Y direction is exponentially increased along the propagation direction g2. Alternatively, the width of the second horn 8 in the Y direction and the width thereof in the Z direction are exponentially increased along the propagation direction g2 in proportion to $\sqrt{e}$. In this way, the cross-sectional area a2 can be exponentially increased.

There is no specific limitation on the external shape of the second horn 8 either as long as having the second space 83 described above. A horn or a cone formed of a plate material such as aluminum or a resin may be used.

The second horn 8 is located such that the first small opening 71 of the first horn 7 and the second small opening 82 of the second horn 8 face each other and such that the first propagation direction g1 of the ultrasonic wave through the first space 73 in the first horn 7 matches the second propagation direction g2 of the ultrasonic wave through the second space 83.

The first horn 7 and the second horn 8 are preferably formed of a material having a significantly different level of acoustic impedance from that of the fluid 4. The reason is that if the ultrasonic wave is transmitted through the material of the first horn 7, the energy density of the ultrasonic wave is reduced. In the case where the fluid 4 is air, a solid material, a resin material and the like are usable. In this embodiment, the first horn 7 and the second horn 8 are formed of aluminum.

A specific example of the shape of the first horn 7 will be described. The first horn 7 formed of aluminum has a thickness of, for example, 0.5 mm. The first large opening 72 has a square shape which is 17 mm long both in the Y direction and the Z direction. In this case, the outer contour of the first horn 7 defining the first large opening 72 is a square which is 18 mm long both in the Y direction and the Z direction.

The first small opening 71 has a rectangular shape which is 1.7 mm long in the Y direction and 17 mm long in the Z direction. The outer contour of the first horn 7 defining the first small opening 71 is a rectangle which is 2.7 mm long in the Y direction and 18 mm long in the Z direction. The first space 73 has a length of 50 mm in the propagation direction g1.

The length of the first space 73 in the propagation direction g1 determines the minimum collectable frequency of the ultrasonic wave. With a greater length of the first space 73, an ultrasonic wave of a lower frequency can be collected. For practical use, where the first space 73 is 50 mm long in the X direction, the first horn 7 can collect an sonic wave of about 1 kHz or greater. By contrast, for ease of use, it is more preferable as the first horn 7 is shorter. However, where the first horn 7 is too short, the ultrasonic wave is more likely to be reflected in the horn. When this occurs, the ultrasonic receiver main bodies 11 cannot detect all the ultrasonic wave propagating through the first space 73. In consideration of these issues, the length of the first space 73 in the propagation direction g1 is set to 50 mm in this embodiment.

The second horn 8 may be designed in a similar manner. For example, the second horn 8 may have the same shape as that of the first horn 7. Alternatively, the first horn 7 and the second horn 8 may be different in length.

The ultrasonic receiver main bodies 11 are provided between the first small opening 71 of the first horn 7 and the second small opening 82 of the second horn 8. In order to obtain a space for installing the ultrasonic receiver main bodies 11, the first horn 7 and the second horn 8 are preferably connected to each other via a third horn 12. The third horn 12 has a third space 13 which has, at two ends thereof, an opening of the same size as that of the first small opening 71 of the first horn 7 and an opening of the same size as that of the second small opening 82 of the second horn 8. A propagation direction of the ultrasonic wave through the third space 13 is on the same line as that of the propagation directions g1 and g2. With the provision of the third space 13, a space passing through the first large opening 72 of the first horn 7 to the second large opening 81 of the second horn 8 is formed. Specifically, the first space 73 and the second space 83 are continuous to each other, and are located to pass through the first horn 7, the third horn 12 and the second horn 8. Herein, the expression "pass through" means that there is no blocking object between the first space 73 and the second space 83 and thus the first space 73, the second space 83 and the third space 13 are provided with certainty. Since there is no blocking object, the ultrasonic wave propagating through the first space 73 advances to the second space 83 while being kept linear, without the propagation direction g1 being changed.

Figure 3:
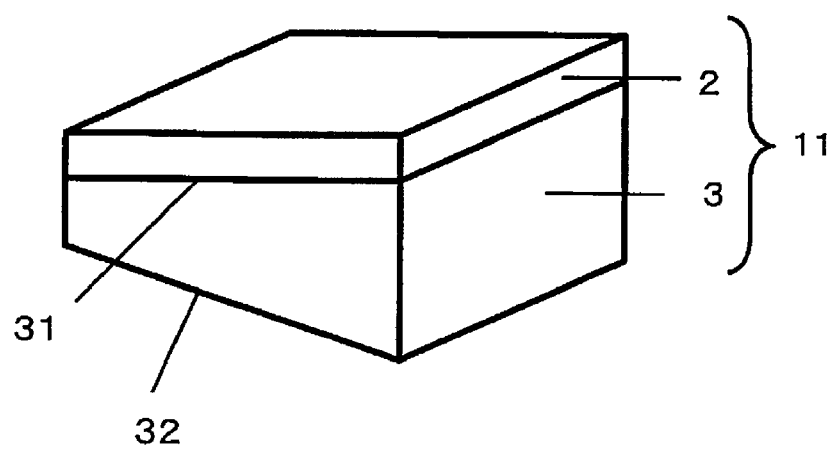
FIG. 3 is an isometric view showing an ultrasonic receiver main body usable for the ultrasonic receiver shown in FIG. 1.

The pair of ultrasonic receiver main bodies 11 each have a second surface area 32 parallel to the propagation direction g1, and detects the ultrasonic wave which is incident on the second surface area 32 after passing through the first space 73. For this purpose, as shown in FIG. 3, the ultrasonic receiver main bodies 11 each include an ultrasonic vibrator 2 and the propagation medium section 3.

The ultrasonic vibrator 2 is formed of a piezoelectric element, and receives an ultrasonic wave by the piezoelectric element. The piezoelectric element is provided with electrodes (not shown), and the electrodes are used to detect a voltage which is generated in the piezoelectric element by the reception of the ultrasonic wave. The piezoelectric element is formed of a material which is known to have a piezoelectric property. A material having a higher level of piezoelectric property improves the ultrasonic receiving efficiency and so is preferable. For example, materials having a high level of piezoelectric property, including piezoelectric ceramics, piezoelectric single crystals, piezoelectric polymers are preferable. As the piezoelectric ceramics, lead zirconate titanate, barium titanate, lead titanate, lead niobium and the like are usable. As the piezoelectric single crystals, lead zirconate titanate single crystal, lithium niobium, quartz and the like are usable. Instead of the piezoelectric element, a known electrostrictive element may be used. As with the piezoelectric element, a material having a larger electrostrictive effect improves the ultrasonic receiving efficiency and so is preferable. The electrodes are formed of a known conductive material. A generally used metal material having a low electric impedance is preferable. In this embodiment, the piezoelectric element is formed of lead zirconate titanate, and the electrodes are formed of silver.

In this embodiment, the ultrasonic vibrator 2 is, for example, a square plate having a thickness of 1 mm and a planar size of 18 mm×18 mm. The ultrasonic vibrator 2 is provided with electrodes on both surfaces in the thickness direction, and is polarized in this direction.

It is preferable that the resonant frequency of the ultrasonic vibrator 2 is sufficiently higher than the frequency of the ultrasonic wave received by the ultrasonic receiver 1. Therefore, the ultrasonic vibrator 2 has a thickness selected such that the ultrasonic vibrator 2 has a sufficiently higher resonant frequency than the frequency of the ultrasonic wave to be received. For example, it is known that in the case where a piezoelectric ceramic material is used for the ultrasonic receiver 2, a strong resonance phenomenon occurs when the sonic velocity of the piezoelectric ceramic material is 3800 m/s and the thickness thereof is ½ wavelength. Accordingly, the resonance frequency of the piezoelectric ceramic material having a thickness of 1 mm is about 1.9 MHz. This is sufficiently higher than the frequency of the ultrasonic wave to be received, which is about 100 kHz. Where the resonant frequency of the ultrasonic vibrator 2 is approximately equal to the frequency of the ultrasonic wave to be received, a high level of receiving sensitivity is obtained at the resonant frequency or the vicinity thereof, but not in the other frequency ranges. In addition, the level of the receiving sensitivity greatly varies in accordance with the frequency. For these reasons, it is difficult to measure the ultrasonic wave accurately.

The propagation medium section 3 takes in the ultrasonic wave which has propagated through the fluid 4 in the first horn 7 and propagates the ultrasonic wave to the ultrasonic vibrator 2. The propagation medium section 3 is preferably formed of a material having little internal loss. The reason is that when the internal loss is large, the ultrasonic wave reaching the ultrasonic vibrator is attenuated and the level of the receiving sensitivity is reduced. The propagation medium section 3 preferably fulfills expression (2) regarding the fluid 4. Where the fluid 4 is air, it is preferable that the density of the propagation medium section 3 is 50 kg/m$^3$ or greater and the sonic velocity therein is 300 m/s or less. The density and the sonic velocity of air at room temperature or the vicinity thereof are 1.12 kg/m$^3$ and 340 m/s, respectively. When these conditions are fulfilled, the reflection at the interface between the propagation medium section 3 and the fluid 4 can be made zero.

In this embodiment, the propagation medium section 3 is formed of a dry gel. A dry gel is a porous material including a solid framework having a size of several nanometers to several micrometers and continuous tiny air pores having an average diameter of about 1 nm to several micrometers contained in the solid framework. Where the density of the dry gel is low, the sonic velocity of the ultrasonic wave propagating through the solid part is extremely small, and also the sonic velocity of the ultrasonic wave propagating through the gas parts in the porous element is also extremely small due to the tiny air pores. Because of such a property, a dry gel at a low density exhibits a very low sonic velocity of 500 m/s or less and has a very low level of acoustic impedance.

For the dry gel, inorganic materials and organic polymer materials are usable, for example. As the inorganic materials forming the solid framework, silicon oxide (silica), aluminum oxide, titanium oxide and the like are usable. As the organic polymer materials forming the solid framework, generally used thermosetting and thermoplastic resins, for example, polyurethane, polyurea, phenol resins, polyacrylamide, methyl polymethacrylate and the like are usable. In this embodiment, the propagation medium section 3 is formed of a silica dry gel.

The silica dry gel is produced by, for example, the following method. First, a mixed solution of tetraethoxysilane (hereinafter, referred to simply as "TEOS"), ethanol and ammonia water is produced. This is gelated to produce a wet gel. A "wet gel" is obtained by filling the pores of the dry gel with a liquid. By removing the liquid part of the wet gel, the silica dry gel is obtained. The liquid part is removed by a supercritical dry method. According to the supercritical dry method, the liquid part of the wet gel is substituted with liquefied carbon dioxide to remove the liquid part by drying in a supercritical state. If the solvent is dried directly from the state where the liquid is contained in the pores of the structure, a large force acts by capillary phenomenon when the solvent is vaporized and thus destroys the structure of the framework. In order to prevent such destruction, the supercritical dry method by which no surface tension acts is used. Thus, the silica dry gel can be obtained without destroying the silica framework. The density of the silica dry gel can be adjusted by changing the ratio of TEOS, ethanol and ammonia water. The sonic velocity changes in accordance with the density of the material forming the propagation medium section 3. In this embodiment, a silica dry gel having a density of 250 kg/m³ and exhibiting a sonic velocity of 145 m/s which fulfill expression (2) is used.

Figure 8:
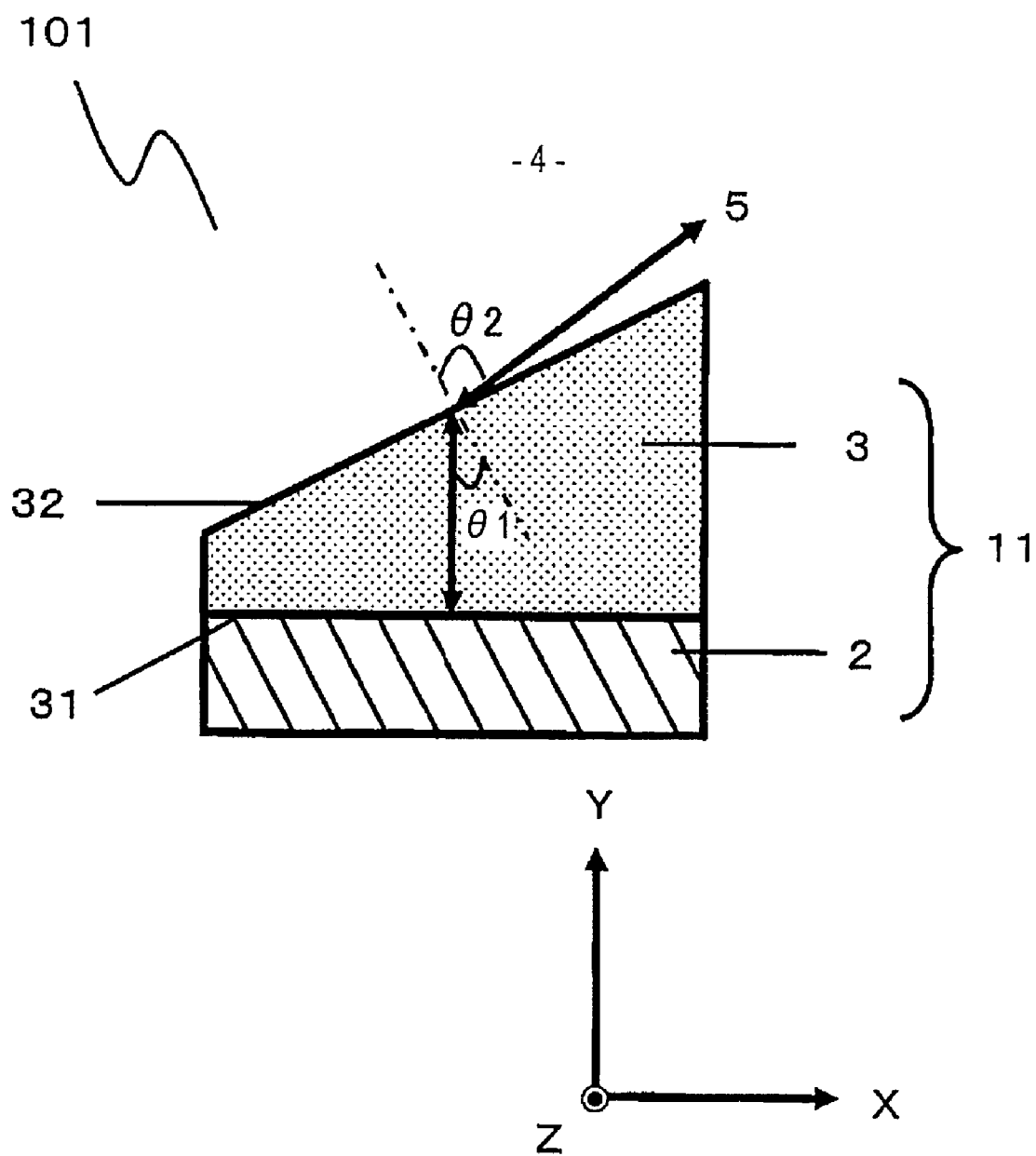
FIG. 8 is a cross-sectional view of an ultrasonic receiver main body usable in Patent Document 1 and an embodiment of the present invention.
Figure 9:
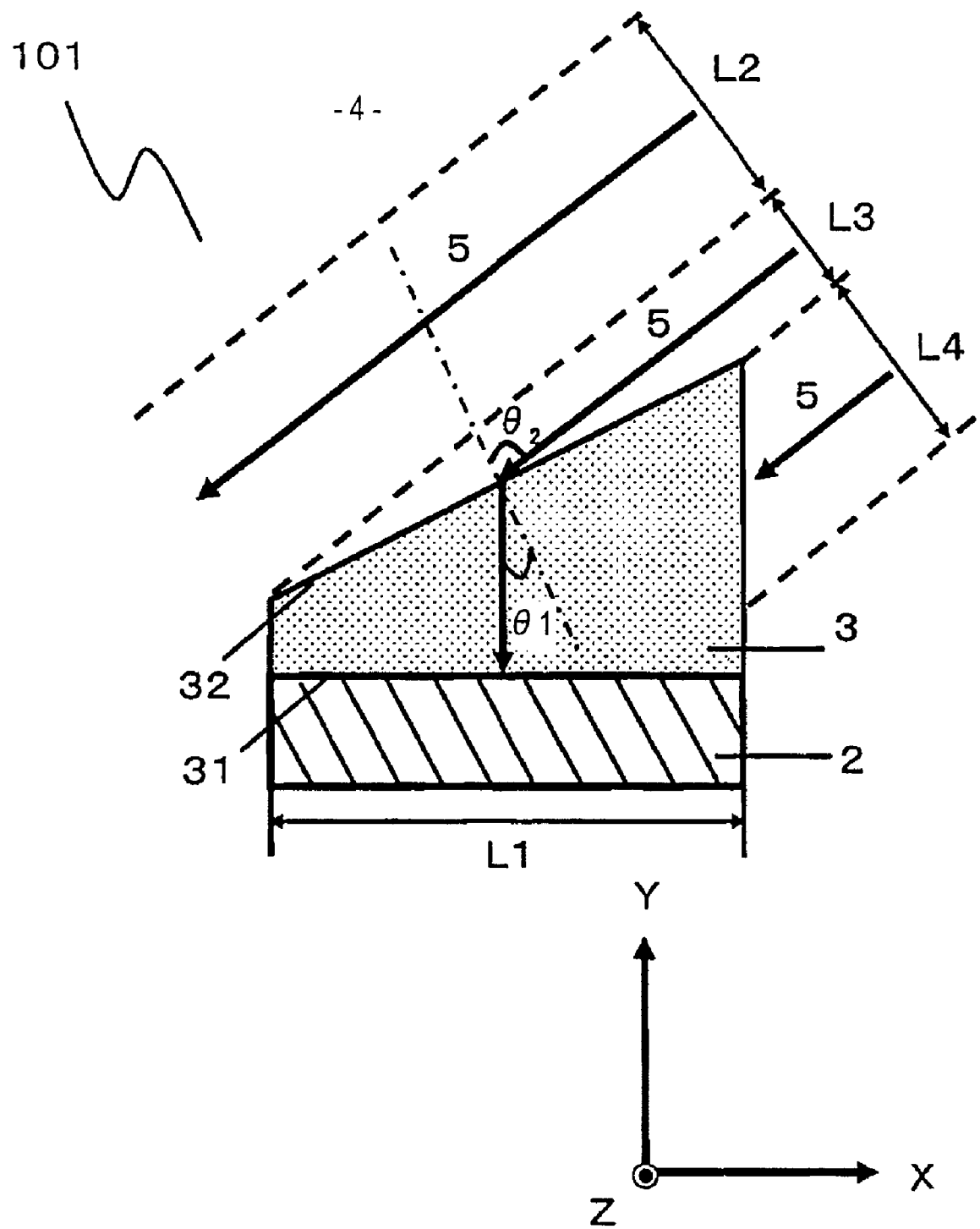
FIG. 9 illustrates a wave receiving area of the ultrasonic receiver main body shown in FIG. 8.

The propagation medium section 3 is set to fulfill expression (4) such that the ultrasonic wave which is refracted and transmitted to the second surface area 32 of the propagation medium section 3 from the fluid 4 is incident vertically on the first surface area 31, which is the wave receiving face of the ultrasonic vibrator 2. Owing to this, the ultrasonic wave reaches the first surface area 31, i.e., the wave receiving face of the ultrasonic vibrator 2, in a phase-matched state. Thus, the voltage generated in the ultrasonic vibrator 2 can be maximized. This maximizes the level of the receiving sensitivity. At this point, as shown in FIG. 8, angle $\theta_1$ made by the first surface area 31 and the second surface area 32 is 24.5 degrees, and angle $\theta_2$ made by the normal to the second surface area 32 and the propagation direction of the ultrasonic wave is about 89 degrees.

In this embodiment, in the YX cross-section shown in FIG. 2, the first surface area 31 as the wave receiving face of the ultrasonic vibrator 2 has a length of 18 mm, and the second surface area 32 of the propagation medium section 3 has a length of 20 mm. Regarding a part for connecting the first surface area 31 and the second surface area 32, a side closer to the first horn 7, i.e., the longer side has a length of 10.2 mm and a side closer to the second horn 8, i.e., the shorter side has a length of 2 mm. The length of the propagation medium section 3 in the Z direction is 18 mm, like in the ultrasonic vibrator 2. The propagation medium section 3 having such a shape is obtained by casting a liquid raw material into a mold of this shape formed of a fluorine-based resin, gelating the raw material, and then removing the gelated raw material.

The first surface area 31 of the propagation medium section 3 formed in this manner is bonded to the wave receiving face of the ultrasonic vibrator 2. Thus, the ultrasonic receiver main body 11 shown in FIG. 3 is obtained. The bonding is conducted using, for example, an epoxy-based adhesive.

The ultrasonic receiver 1 is produced by, for example, the following method.

Figure 4:
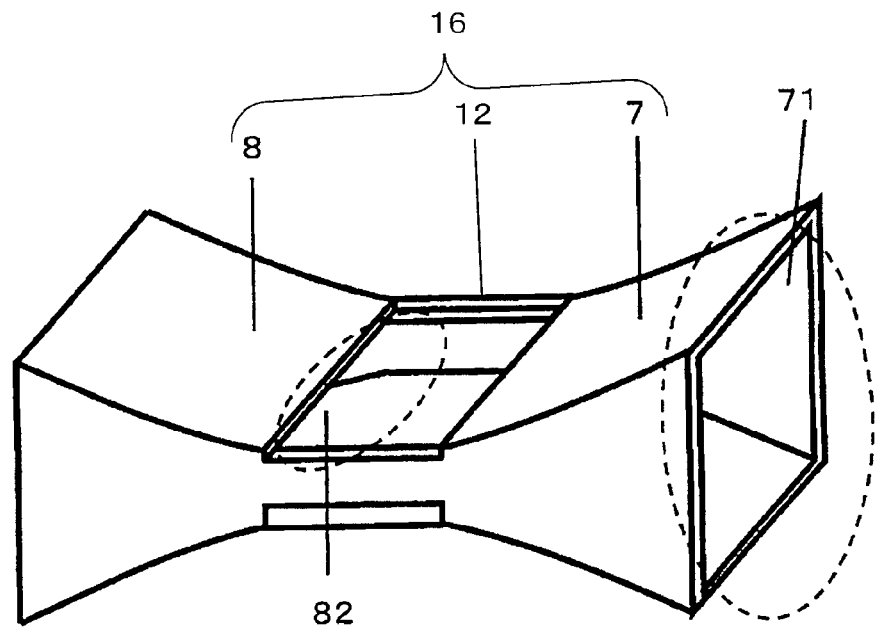
FIG. 4 is an isometric view showing an example of parts included in the ultrasonic receiver shown in FIG. 1.
Figure 4:
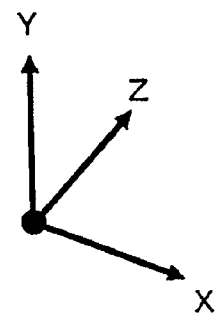

First, a horn main body 16 formed of, for example, aluminum and including the first horn 7, the second horn 8 and the third horn 12 integrally molded is prepared. As shown in FIG. 4, the third horn 12 has an opening in plane XZ for connecting the pair of ultrasonic receiver main bodies 11. Two faces of the third horn 12 which are parallel to plane YZ are integrally bonded to the first horn 7 and the second horn 8, respectively.

The second surface areas 32 of the propagation medium sections 3 are positionally aligned to the openings of the third horn 12 to attach the ultrasonic receiver main bodies 11 to the horn main body 16. At this point, the interval in the Y direction between the propagation medium sections 3 facing each other is set to 1.7 mm, which is half of the wavelength of the ultrasonic wave. Since the interval is set to half of the wavelength of the ultrasonic wave, the ultrasonic wave propagating in the third horn 12 can be made closer to a plane wave and thus the ultrasonic wave is prevented from being disturbed by the first horn 7. The ultrasonic receiver main bodies 11 are located such that the longer side of each propagation medium section 3 in plane XY is closer to the first horn 7.

Figure 5:
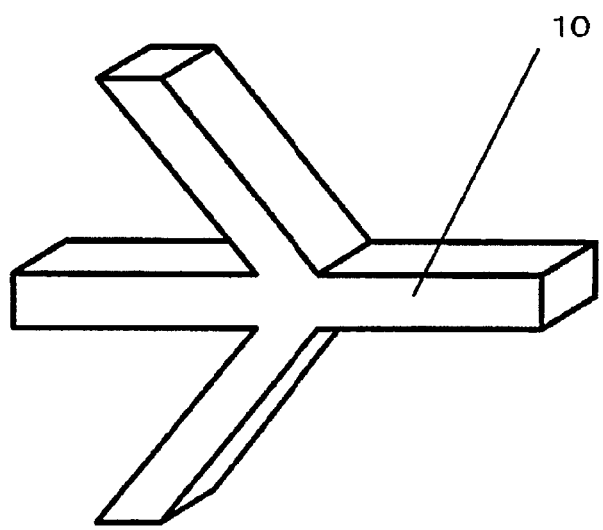
FIG. 5 is an isometric view of an attaching member usable for the ultrasonic receiver shown in FIG. 1.

After the positional alignment, a connecting member 10 shown in FIG. 5 is used to assemble the horn main body 16 and the ultrasonic receiver main bodies 11 in plane XY. The parts to be assembled are bonded together with an adhesive. For the bonding, an epoxy-based adhesive is usable, for example. In this embodiment, the horn main body 16 is integrally molded of aluminum, but may be molded by other methods. Alternatively, the first horn 7, the second horn 8 and the third horn 12 may be molded as independent parts and then bonded together. The ultrasonic vibrator 1 is produced in this manner.

Now, with reference to FIG. 2, an operation of the ultrasonic vibrator 1 will be described. The ultrasonic wave 5 to be detected is incident on the first large opening 72 and propagates parallel to the propagation direction g1. As the ultrasonic wave further propagates, the sound pressure is raised by the first horn 7. The ultrasonic wave represented with the arrows in FIG. 2 is a portion of the ultrasonic wave incident on the first large opening 72. In actuality, the ultrasonic wave is incident on the entirety of the first large opening 72 and is converged without being unnecessarily reflected by the side faces defining the first space 73.

The ultrasonic wave 5 propagates through the first space 73 while being converged, passes through the first small opening 71 and reaches the second surface areas 32 of the ultrasonic receiver main bodies 11. Among the ultrasonic wave which has reached the second surface areas 32, an ultrasonic wave component traveling in a direction which makes angle $\theta_2$ fulfilling expressions (3) and (4) with the normal to the second surface area 32 (where $\theta_1$ is 24.5 degrees, $\theta_2$ is about 89 degrees) propagates to the propagation medium sections 3 as represented with solid arrows A1. The ultrasonic wave of arrows A1 transmitted to the propagation medium sections 3 reaches the ultrasonic vibrators 2 and is converted to an electric signal. The ultrasonic receiver main bodies 11 which detect the ultrasonic wave are refraction propagation type ultrasonic receivers as suggested above, and so suppress the reflection and can detect the ultrasonic wave at high efficiency. The ultrasonic wave which has reached the second surface areas 32 is converged and has a high sound pressure. Therefore, the ultrasonic receiver main bodies 11 can detect the ultrasonic wave at high sensitivity.

The ultrasonic wave of arrow A2 which did not reach the second surface areas 32 propagates from the second small opening 82 through the second space 83. Since the cross-sectional area of the second space 83 gradually increases, the acoustic impedance of the fluid 4' in the second space 83 gradually decreases. This prevents the ultrasonic wave of arrow A2 from being reflected in the second space 83 by the mismatching of impedance.

The ultrasonic wave of arrow A2 which has reached the second large opening 81 goes outside from the second large opening 81. Since the cross-sectional area of the second space 83 is larger in the vicinity of the second large opening 81, the acoustic impedance of the fluid 4' approximately matches the acoustic impedance of the outside. Therefore, the ultrasonic wave of arrow A2 goes out without being reflected by the mismatching of impedance.

Accordingly, the ultrasonic receiver 1 of the present invention can detect an ultrasonic wave at high sensitivity and high efficiency. The ultrasonic wave which was not detected by the ultrasonic receiver main bodies is not reflected by an end portion or the like and thus is never detected by the ultrasonic receiver main bodies 11. Therefore, the ultrasonic wave can be received or detected accurately.

As described above, in the ultrasonic receiver 1 of the present invention, the second horn 8 is used to take in the ultrasonic wave, which was not detected by the ultrasonic receiver main bodies, from the second small opening 82 and output the ultrasonic wave outside from the second large opening 83. Such a function is made necessary because unnecessary reflected waves are caused in a structure in which the ultrasonic wave to be detected is incident on a face parallel to the propagation direction of the ultrasonic wave. Therefore, the present invention is based on a totally different conception from the ultrasonic sensor disclosed in Patent Document 2 including two horns for receiving an ultrasonic wave from two directions, or a sonic wave transducer disclosed in Patent Document 3 including a horn for improving the directivity and a base for allowing the piezoelectric element to vibrate easily.

Figure 6:
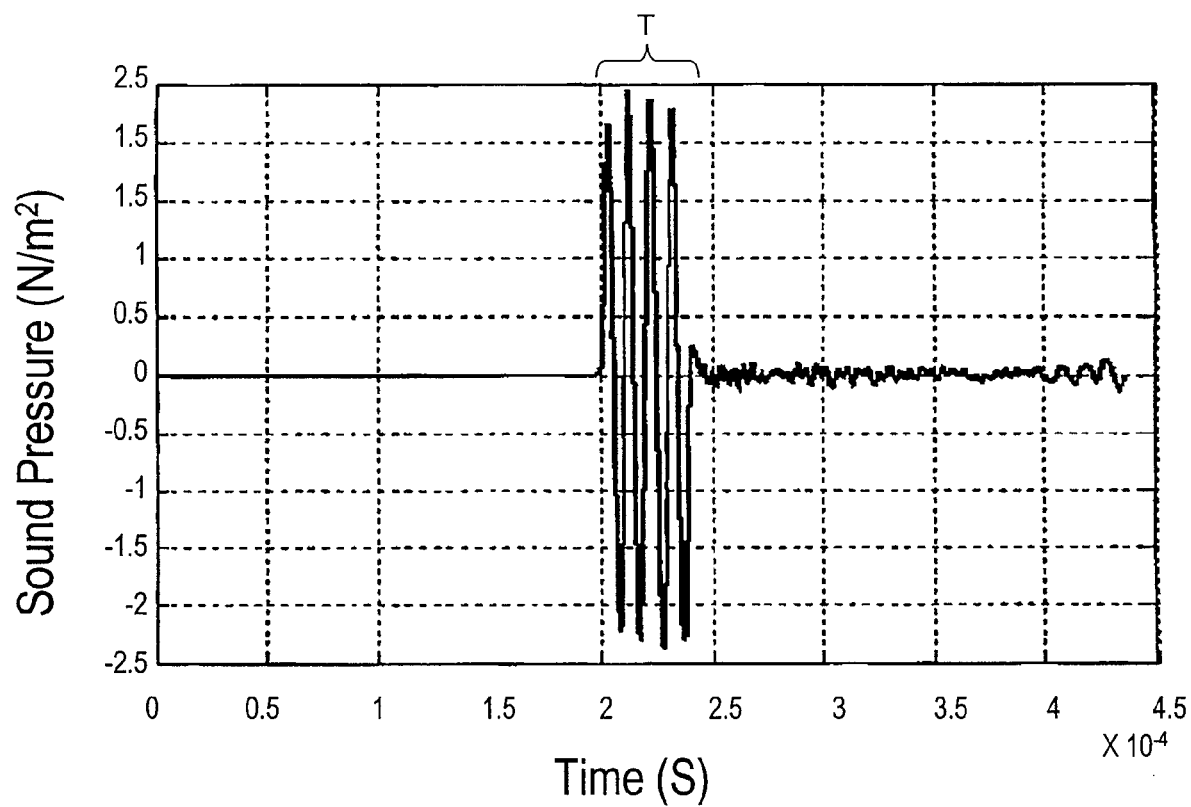
FIG. 6 is a graph showing a result of detecting an ultrasonic wave using the ultrasonic receiver shown in FIG. 1.

FIG. 6 shows a result of receiving, by the ultrasonic receiver 1, a 100 kHz four-peak burst ultrasonic wave propagating from the positive X axial side. In FIG. 6, the horizontal axis represents the time, and the vertical axis represents an over-time change in the sound pressure at point A in FIG. 2. As shown in FIG. 6, only an ultrasonic wave T having four peaks is detected, with almost no unnecessary ultrasonic waves by reflection being detected. This demonstrates that the present invention realizes accurate receiving or detection of an ultrasonic wave.

Figure 7:
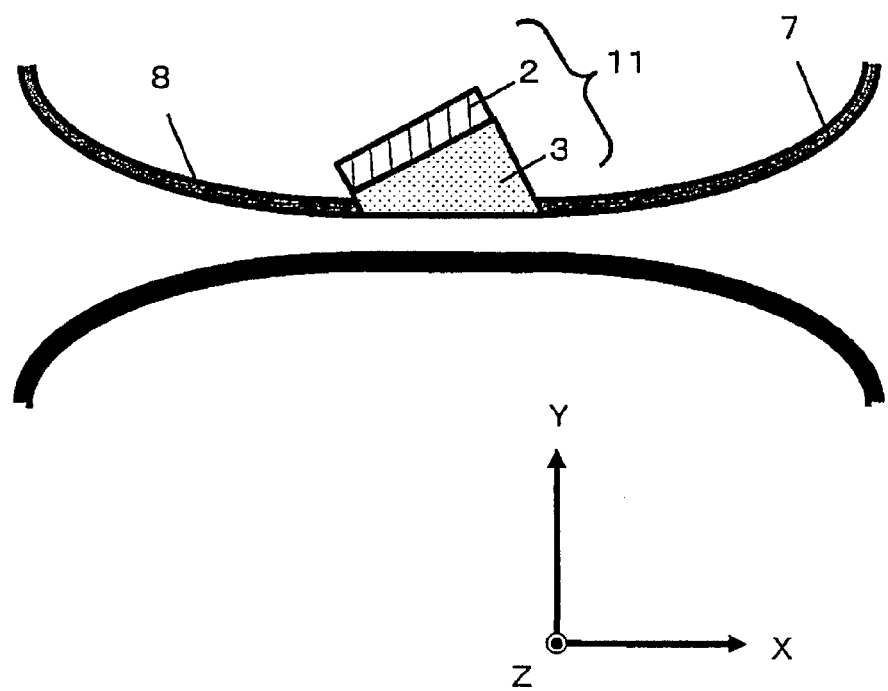
FIG. 7 is a cross-sectional view showing an ultrasonic receiver in another embodiment according to the present invention.

In this embodiment, the ultrasonic receiver 1 includes a pair of ultrasonic receiver main bodies 11. There is no specific limitation on the number of the ultrasonic receiver main bodies (body) 11. An ultrasonic receiver including one ultrasonic receiver main body as shown in FIG. 7 may be implemented, or an ultrasonic receiver including three or more ultrasonic receiver main bodies may be implemented.

The second space 83 of the second horn 8 is not limited to having the above-described shape. The second space 83 may be defined by any other shape which allows the acoustic impedance of the fluid 4' in the second space 83 to gradually change in accordance with the propagation direction g2.

The function of the second horn is to gradually decrease the acoustic impedance of the fluid 4 filling the narrow space in the vicinity of the ultrasonic receiver main bodies 11 and to match this acoustic impedance with the acoustic impedance of the fluid in the completely opened space. Such a function can be realized also by a method which does not change the cross-sectional area of the space.

Accordingly, an ultrasonic receiver according to the present invention can be implemented by using an acoustic impedance transformer having a structure providing such a function, instead of the second horn.

INDUSTRIAL APPLICABILITY

An ultrasonic receiver according to the present invention is capable of receiving an ultrasonic wave at high sensitivity and high accuracy, and is preferably applicable for an ultrasonic receiver or the like usable for distance measurement, object detection, flow rate measurement, robot control or the like.

The invention claimed is:

1. An ultrasonic receiver, comprising:
   a first horn having a first large opening which is an ultrasonic incidence end and a first small opening which is an ultrasonic outgoing end;
   a second horn having a second small opening which is an ultrasonic incidence end and a second large opening which is an ultrasonic outgoing end, the second horn being located such that the first small opening of the first horn and the second small opening of the second horn face each other, and such that a first propagation direction of an ultrasonic wave propagating in the first horn and a second propagation direction of the ultrasonic wave propagating in the second horn match each other; and
   at least one ultrasonic receiver main body provided between the first small opening of the first horn and the second small opening of the second horn, the ultrasonic receiver including a surface parallel to the first propagation direction and detecting the ultrasonic wave which has propagated in the first horn and then is incident on the parallel surface;
   wherein:
   a space in the first horn in which the ultrasonic wave propagates has a cross-sectional area, vertical to the first propagation direction, which decreases from the first large opening toward the first small opening; and
   a space in the second horn in which the ultrasonic wave propagates has a cross-sectional area, vertical to the second propagation direction, which increases from the second small opening toward the second large opening.

2. The ultrasonic receiver of claim 1, which has a space passing through the first large opening of the first horn to the second large opening of the second horn.

3. The ultrasonic receiver of claim 2, wherein in the first horn, the cross-sectional area, vertical to the first propagation direction, of the space through which the ultrasonic propagates exponentially decreases along a propagation direction from the first large opening to the first small opening.

4. The ultrasonic receiver of claim 3, wherein in the second horn, the cross-sectional area, vertical to the second propagation direction, of the space through which the ultrasonic propagates exponentially increases along a propagation direction from the second small opening to the second large opening.

5. The ultrasonic receiver of claim 4, wherein the at least one ultrasonic receiver main body includes:
   an ultrasonic vibrator having a wave receiving face; and
   a propagation medium section having a first surface area and a second surface area;
   wherein the first surface area of the propagation medium section is bonded with the wave receiving face of the ultrasonic vibrator, and the first surface area of the propagation medium section forms the parallel surface.

6. The ultrasonic receiver of claim 5, wherein the relationship of $(\rho_2/\rho_1) < (C_1/C_2) < 1$ is fulfilled where $\rho_1$ and $\rho_2$ are densities of the propagation medium section and a fluid filling a space around the at least one ultrasonic receiver main body, and $C_1$ and $C_2$ are sonic velocities of the ultrasonic wave in the propagation medium section and the fluid filling the space.

7. The ultrasonic receiver of claim 6, wherein the propagation medium section is formed of an dry gel formed of an inorganic material or an organic polymer material.

8. An ultrasonic receiver, comprising:
   a first horn having a first large opening which is an ultrasonic incidence end and a first small opening which is an ultrasonic outgoing end;
   at least one ultrasonic receiver main body provided adjacent to the first small opening, the ultrasonic receiver including a surface parallel to a first propagation direction in which an ultrasonic wave propagates in the first horn, and detecting the ultrasonic wave which has propagated in the first horn and then is incident on the parallel surface; and
   an acoustic impedance transformer for holding a fluid fulfilling a space around the at least one ultrasonic receiver main body such that an acoustic impedance of the fluid gradually changes, the acoustic impedance transformer being provided such that the ultrasonic receiver main body is held between the first horn and the acoustic impedance transformer;
   wherein a space in the first horn in which the ultrasonic wave propagates has a cross-sectional area, vertical to the first propagation direction, which decreases from the first large opening toward the first small opening.

* * * * *

UNITED STATES PATENT AND TRADEMARK OFFICE
CERTIFICATE OF CORRECTION

PATENT NO. : 7,565,842 B2
APPLICATION NO. : 11/996529
DATED : July 28, 2009
INVENTOR(S) : Hidetomo Nagahara, Masahiko Hashimoto and Takehiko Suginouchi It is certified that error appears in the above-identified patent and that said Letters Patent is hereby corrected as shown below:

Column 16, lines 17-18 and 22-23,
"ultrasonic propagates" should read -- ultrasonic wave propagates --; and Line 42, "an dry" should read -- a dry --.

Signed and Sealed this

Eighth Day of December, 2009

David J. Kappos
*Director of the United States Patent and Trademark Office*